US 6,745,902 B2

(12) United States Patent
Lynn et al.

(10) Patent No.: US 6,745,902 B2
(45) Date of Patent: Jun. 8, 2004

(54) BLOOD COLLECTION SYSTEMS INCLUDING AN INTEGRAL, FLEXIBLE FILTER

(75) Inventors: Daniel R Lynn, Spring Grove, IL (US); Julian C Breillatt, Mundelein, IL (US); John C Burnham, Lake Zurich, IL (US); David B. Howard, Crystal Lake, IL (US); Allen R Wons, Antioch, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 10/159,442

(22) Filed: May 31, 2002

(65) Prior Publication Data

US 2002/0148764 A1 Oct. 17, 2002

Related U.S. Application Data (62) Division of application No. 09/593,782, filed on Jun. 14, 2000, now Pat. No. 6,422,397, which is a continuation-in-part of application No. 09/498,085, filed on Feb. 4, 2000, now Pat. No. 6,367,634, which is a continuation-in-part of application No. 08/697,270, filed on Aug. 21, 1996, now Pat. No. 6,032,807, which is a continuation of application No. 08/558,458, filed on Nov. 16, 1995, now abandoned, which is a continuation of application No. 08/392,297, filed on Feb. 22, 1995, now abandoned, which is a continuation of application No. 08/173,608, filed on Dec. 22, 1993, now abandoned.

(51) Int. Cl.[7] .................. B01D 29/56; B01D 29/58; B01D 36/00
(52) U.S. Cl. .................. 210/489; 210/252; 210/257.1; 210/483; 210/488
(58) Field of Search .................. 210/252, 257.1, 210/453, 488, 483, 489, 496; 156/272.2, 273.7

(56) References Cited

U.S. PATENT DOCUMENTS

| | | |
|---|---|---|
| 3,506,130 A | 4/1970 | Shaye |
| 3,747,769 A | 7/1973 | Brumfield |
| 4,025,618 A | 5/1977 | Garber et al. |
| 4,035,304 A | 7/1977 | Watanabe |
| 4,066,556 A | 1/1978 | Vaillancourt |
| 4,113,627 A | 9/1978 | Leason |
| 4,157,967 A | 6/1979 | Meyst et al. |
| 4,170,056 A | 10/1979 | Meyst et al. |
| 4,193,876 A | 3/1980 | Leeke et al. |
| 4,211,825 A | 7/1980 | Shipman |
| 4,234,026 A | 11/1980 | Bayham |
| 4,235,233 A | 11/1980 | Mouwen |
| 4,240,481 A | 12/1980 | Bayham |
| 4,268,338 A | 5/1981 | Peterson |
| 4,305,443 A | 12/1981 | Bayham |
| 4,380,484 A | 4/1983 | Repik et al. |
| 4,417,753 A | 11/1983 | Bacehowski et al. |
| 4,425,177 A | 1/1984 | Shinno |
| 4,437,472 A | 3/1984 | Naftulin |
| 4,460,366 A | 7/1984 | Shinno |

(List continued on next page.)

FOREIGN PATENT DOCUMENTS

| | | |
|---|---|---|
| EP | 0155003 A2 | 9/1985 |
| EP | 0328038 A2 | 8/1989 |
| EP | 0365676 A1 | 5/1990 |
| EP | 0 365 676 | 5/1990 |

(List continued on next page.)

OTHER PUBLICATIONS

Excerpts from Opposition involving EP 684,867 (European Counterpart of Lynn US 5,591,337) including (1) Notice of Opposition; (2) Response to Opposition; (3) Statement Replying to Response; (4) Reply to Statement in Response; and (5) Opposition Decision.
Opposition Decision, European Patent Office, May 15, 2001; Ref. No. BAXR/M7328EP EP 684867.

*Primary Examiner*—John Kim
(74) *Attorney, Agent, or Firm*—Daniel D. Ryan; Bradford R. L. Price; Michael C. Mayo (57) ABSTRACT

Blood collection systems include an integral flexible filter to remove leukocytes from blood components.

5 Claims, 12 Drawing Sheets

U.S. PATENT DOCUMENTS

| | | |
|---|---|---|
| 4,466,888 A | 8/1984 | Verkaart |
| 4,482,585 A | 11/1984 | Ohodaira et al. |
| 4,493,705 A | 1/1985 | Gordon et al. |
| 4,507,123 A | 3/1985 | Yoshida |
| 4,539,793 A | 9/1985 | Malek |
| 4,707,402 A | 11/1987 | Thorsrud |
| 4,767,541 A | 8/1988 | Wisdom |
| 4,770,295 A | 9/1988 | Carveth et al. |
| 4,798,578 A | 1/1989 | Ranford |
| 4,857,129 A | 8/1989 | Jensen et al. |
| 4,863,603 A | 9/1989 | Lehmann et al. |
| 4,892,603 A | 1/1990 | Lustig et al. |
| 4,892,604 A | 1/1990 | Measells et al. |
| 4,894,107 A | 1/1990 | Tse et al. |
| 4,900,389 A | 2/1990 | Schnell et al. |
| 4,900,441 A | 2/1990 | Graus et al. |
| 4,950,347 A | 8/1990 | Futagawa |
| 4,954,251 A | 9/1990 | Barnes et al. |
| 4,976,851 A | 12/1990 | Tanokura et al. |
| 4,997,577 A | 3/1991 | Stewart |
| 5,049,146 A | 9/1991 | Bringham et al. |
| 5,055,198 A | 10/1991 | Shettigar |
| 5,066,290 A | 11/1991 | Measells et al. |
| 5,180,504 A | 1/1993 | Johnson et al. .......... 210/257.1 |
| 5,190,657 A | 3/1993 | Heagle et al. |
| 5,225,014 A | 7/1993 | Ogata et al. |
| 5,269,924 A | 12/1993 | Rochat |
| 5,306,269 A | 4/1994 | Lewis et al. |
| 5,316,678 A | 5/1994 | Heaslip |
| 5,360,498 A | 11/1994 | Blomqvist et al. |
| 5,420,962 A | 5/1995 | Bakke |
| 5,435,878 A | 7/1995 | Delmar et al. |
| 5,449,428 A | 9/1995 | Desmarais et al. |
| 5,489,385 A | 2/1996 | Raabe et al. |
| 5,507,904 A | 4/1996 | Fisher et al. |
| 5,527,472 A | 6/1996 | Bellotti et al. .......... 210/257.1 |
| 5,556,541 A | 9/1996 | Ruschke |
| 5,575,880 A | 11/1996 | Strassberg |
| 5,580,349 A | 12/1996 | Thor et al. |
| 5,583,577 A | 12/1996 | Tsukagoshi |
| 5,591,337 A | 1/1997 | Lynn et al. |
| 5,601,730 A | 2/1997 | Page et al. |
| 5,683,768 A | 11/1997 | Shang et al. |
| 5,688,460 A | 11/1997 | Ruschke |
| 5,724,988 A | 3/1998 | Dennehey et al. |
| 5,728,249 A | 3/1998 | Kinsey, Jr. et al. |
| 5,728,306 A | 3/1998 | Breillatt, Jr. et al. |
| 5,736,719 A | 4/1998 | Lawson et al. |
| 5,772,880 A | 6/1998 | Lynn et al. |
| 5,858,016 A | 1/1999 | Bacehowski et al. |
| 5,976,300 A | 11/1999 | Buchanan et al. |
| 6,032,807 A | 3/2000 | Sternberg et al. |

FOREIGN PATENT DOCUMENTS

| | | |
|---|---|---|
| EP | 0 516 846 | 12/1992 |
| EP | 0 521 222 | 1/1993 |
| EP | 0 525 493 | 2/1993 |
| EP | 0526678 B1 | 2/1993 |
| EP | 0526678 A1 | 2/1993 |
| EP | 0614675 A1 | 9/1994 |
| EP | 0 654 303 | 5/1995 |
| EP | 0679490 A2 | 11/1995 |
| EP | 684867 | 12/1995 |
| WO | WO95/07818 | 3/1995 |
| WO | WO95/17237 | 6/1995 |

BLOOD COLLECTION SYSTEMS INCLUDING AN INTEGRAL, FLEXIBLE FILTER

RELATED APPLICATIONS

This application is a division of application Ser. No. 09/593,782 filed Jun. 14, 2000 (now U.S. Pat. No. 6,422, 397), which is a continuation-in-part of application Ser. No. 09/498,085 filed Feb. 4, 2000 (now U.S. Pat. No. 6,367, 634), which application is also a continuation-in-part of U.S. patent application, Ser. No. 08/697,270, filed Aug. 21, 1996 (now U.S. Pat. No. 6,032,807), which is a continuation of U.S. patent application Ser. No. 08/558,458, filed Nov. 16, 1995 (now abandoned), which is a continuation of U.S. patent application Ser. No. 08/392,297, filed Feb. 22, 1995 (now abandoned), which is a continuation of U.S. patent application Ser. No. 08/173,608, filed Dec. 22, 1993 (now abandoned).

FIELD OF THE INVENTION

The invention generally relates to blood collection and processing systems and methods.

BACKGROUND OF THE INVENTION

Systems composed of multiple, interconnected plastic bags have met widespread use and acceptance in the collection, processing and storage of blood components. Using these systems, whole blood is collected and separated into its clinical components (typically red blood cells, platelets, and plasma). The components are individually stored and used to treat a multiplicity of specific conditions and diseased states.

Before storing blood components for later transfusion, it is believed to be desirable to minimize the presence of impurities or other materials that may cause undesired side effects in the recipient. For example, because of possible reactions, it is generally considered desirable to remove substantially all the leukocytes from blood components before storage, or at least before transfusion.

Filtration is conventionally used to accomplish leukoreduction. Systems and methods for reducing the number of leukocytes by filtration in multiple blood bag configurations are described, e.g., in Stewart U.S. Pat. No. 4,997,577, Stewart et al. U.S. Pat. No. 5,128,048, Johnson et al. U.S. Pat. No. 5,180,504, and Bellotti et. al. U.S. Pat. No. 5,527, 472.

SUMMARY OF THE INVENTION

The invention provides a blood collection system comprising a container for holding blood and a filter communicating with the container. The filter includes first and second flexible sheets comprising a meltable material and a depth filter medium comprising a meltable material. A peripheral seal joins the sheets directly to the filter medium to encapsulate the filter medium between the first and second sheets. The seal comprises a commingled melted matrix comprising material of the sheets and material of the filter medium.

In a preferred embodiment, the filter medium removes leukocytes from blood.

Other features and advantages of the invention will become apparent upon review of the following description, drawings, and appended claims.

The invention is not limited to the details of the construction and the arrangements of parts set forth in the following description or shown in the drawings. The invention can be practiced in other embodiments and in various other ways. The terminology and phrases are used for description and should not be regarded as limiting.

DESCRIPTION OF THE PREFERRED EMBODIMENTS

Figure 1:
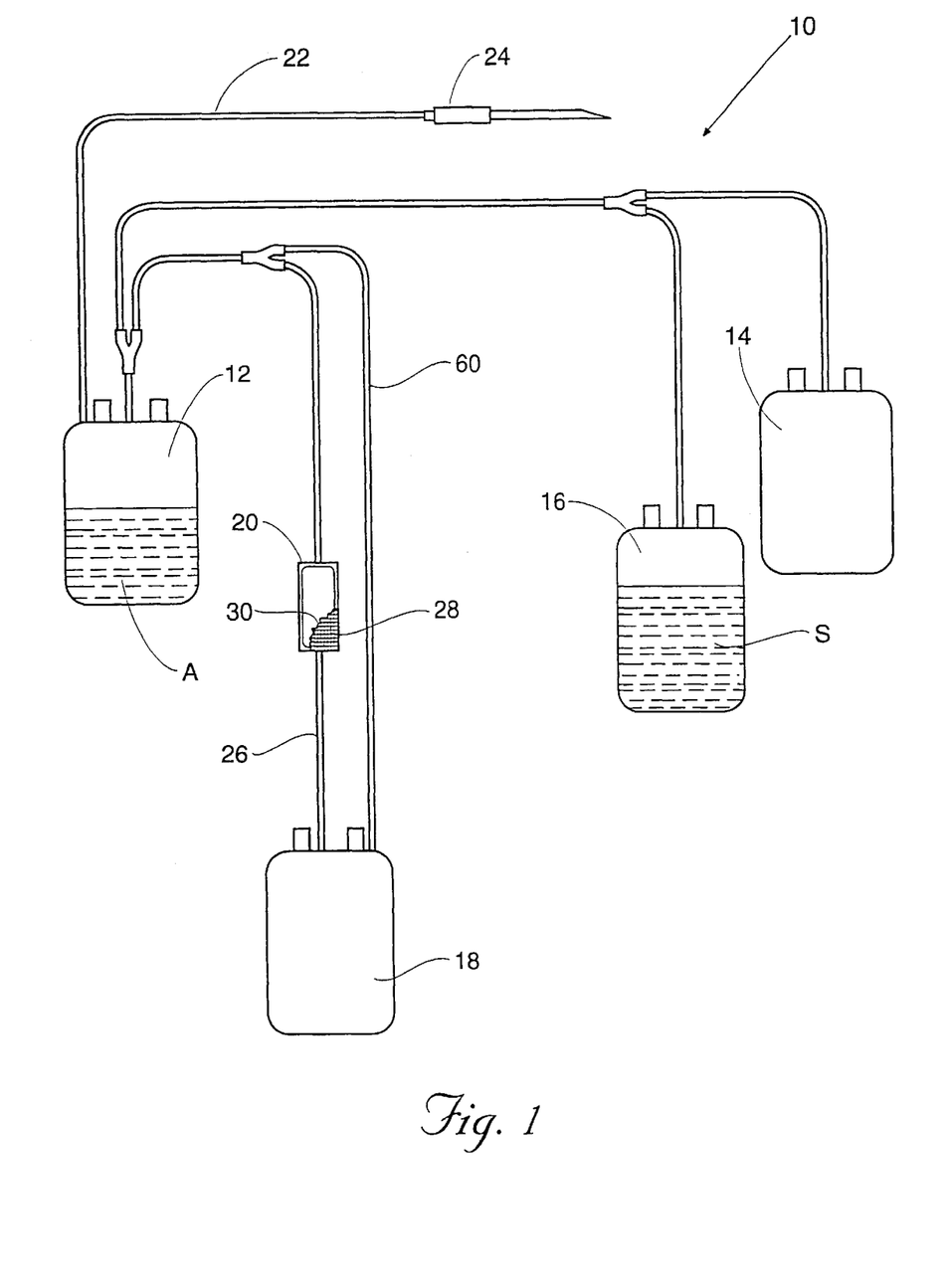
FIG. 1 is a schematic view of a blood collection and storage system that includes an integral flexible filter that removes leukocytes from red blood cells.

FIG. 1 shows a manual blood collection and storage system 10 having an integral flexible filter 20. The system 10 provides red blood cells for long term storage that are substantially free of leukocytes. The system 10 also provides platelet concentrate and the platelet-poor plasma for long term storage. The blood collection and storage assembly 10, once sterilized, constitutes a sterile, "closed" system, as judged by the applicable standards in the United States. The system 10 is a disposable, single use item.

As shown in FIG. 1, the system 10 includes a primary bag 12 and three transfer bags or containers 14, 16, and 18. Like the flexible filter 20, the transfer bags 14, 16, and 18 are integrally attached to the system 10. In use, the system 10 is manipulated in conventional ways. The primary bag 12 (which is also called a donor bag) receives whole blood from a donor through integrally attached donor tube 22 that carries an phlebotomy needle 24. A suitable anticoagulant A is contained in the primary bag 12. The whole blood is centrifugally separated by convention means inside the primary bag 12 into red blood cells and platelet-rich plasma. Leukocytes dwell in the interface between the red blood cells and platelet-rich plasma.

The transfer bag 14 is intended to receive platelet-rich plasma separated from the whole blood collected in the primary bag 12. Attempts are made when transferring the platelet-rich plasma out of the primary bag 12 to keep as many leukocytes in the primary bag 12 as possible. The transfer of platelet-rich plasma into the transfer bag 14 leaves the red blood cells and the leukocytes behind in the primary bag 12.

The transfer bag 16 contains a suitable storage solution S for red blood cells. One such solution is disclosed in Grode et al U.S. Pat. No. 4,267,269, which is sold by Baxter Healthcare Corporation under the brand name ADSOL® Solution. The storage solution S is transferred into the primary bag 12 after transfer of the platelet-rich plasma into the transfer bag 14.

The platelet-rich plasma is centrifugally separated by conventional means in the transfer bag 14 into platelet concentrate and platelet-poor plasma. The platelet-poor plasma is transferred into the transfer bag 16, which is now emptied of storage solution S. The transfer bag 16 serves as the storage container for the platelet-poor plasma. The transfer bag 14 serves as its storage container for the platelet concentrate.

The storage solution S is mixed with the red blood cells and leukocytes remaining in the primary bag 12. The mixture of storage solution S, red blood cells, and leukocytes is transferred from the primary bag 12 through tubing 26. The tubing 26 carries in-line the integral, flexible filter 20. The flexible filter 20 includes a filtration medium 28 contained within a housing 30. The filtration medium is selected to remove leukocytes from red blood cells.

The leukocyte-reduced red blood cells enter the transfer bag 18. The transfer bag 18 serves as the storage container for the leukocyte-reduced red blood cells.

The bags and tubing associated with the processing system 10 can all be made from conventional approved medical grade plastic materials, such as polyvinyl chloride plasticized with di-2-ethylhexyl-phthalate (PVC-DEHP). The bags are formed using conventional heat sealing technologies, e.g., radio frequency (RF) heat sealing.

Alternatively, since the transfer bag 14 is intended to store the platelet concentrate, it can be made of polyolefin material (as disclosed in Gajewski et al U.S. Pat. No. 4,140,162) or a polyvinyl chloride material plasticized with tri-2-ethylhexyl trimellitate (TEHTM). These materials, when compared to DEHP-plasticized polyvinyl chloride materials, have greater gas permeability that is beneficial for platelet storage.

The flexible filter 20, like the rest of the system 10, is a disposable, single use item. Also, like the rest of the system 10, the filter housing 30 is made using conventional approved medical grade plastic materials. Furthermore, like the rest of the system 10, the filter housing 30 is formed using conventional radio frequency heat sealing technology. The filter 20, being flexible, facilitates handling and reduces the incidence of damage to other components of the system 10 during centrifugal processing.

In the illustrated embodiment (see FIG. 2), the filter housing 30 comprising first and second sheets 32 and 34 of medical grade plastic material, such as polyvinyl chloride plasticized with di-2-ethylhexyl-phthalate (PVC-DEHP). Other medical grade plastic materials can be used that are not PVC and/or are DEHP-free, provided that the material heats and flows when exposed to radio frequency energy.

Figure 2:
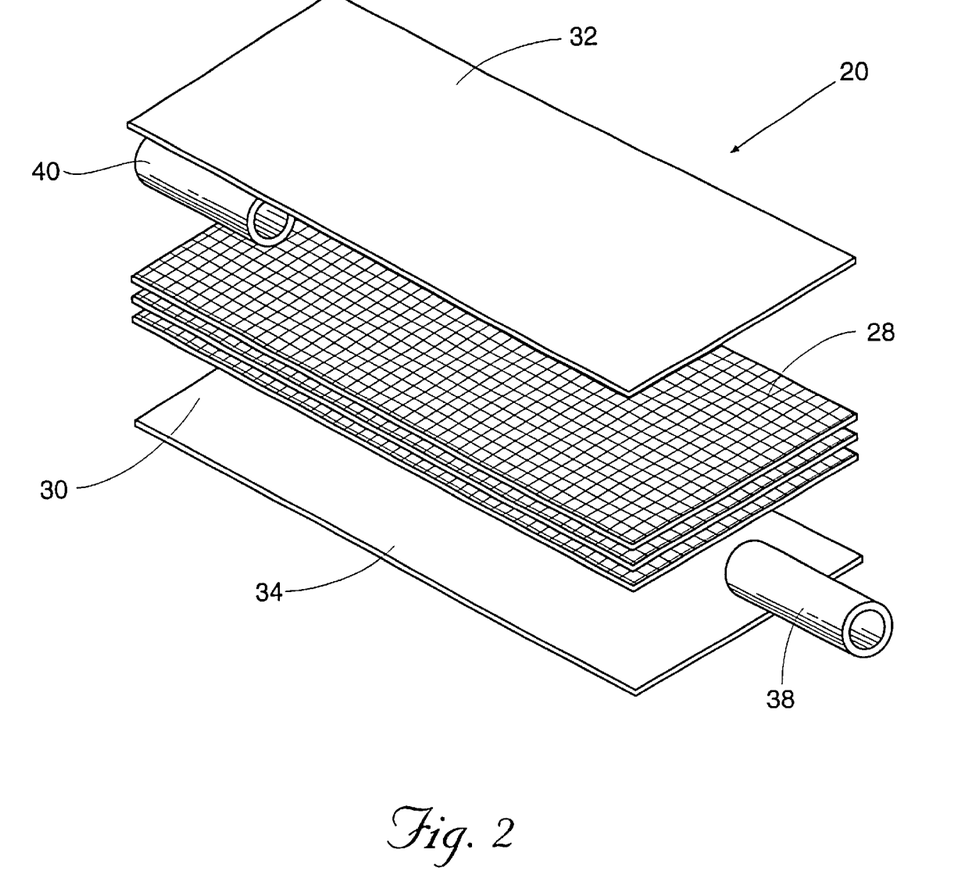
FIG. 2 is an exploded perspective view of the integral flexible filter that forms a part of the system shown in FIG. 1, showing inlet and outlet ports that pass through the unitary peripheral seal.

The filtration medium 28 is made from a fibrous material, which is sandwiched between the sheets 32 and 34. The filtration medium 28 can be arranged in a single layer or in a multiple layer stack. The medium 28 can include melt blown or spun bonded synthetic fibers (e.g., nylon or polyester or polypropylene), semi-synthetic fibers, regenerated fibers, or inorganic fibers. In use, the medium 28 removes leukocytes by depth filtration.

In the illustrated embodiment, the filtration medium 28 comprises, in the blood flow direction, a prefilter region, a main filter region, and a postfilter region. The prefilter and postfilter are made of fibrous material (e.g., polyethylene) having a pore size and fiber diameter not suited for leukocyte removal. Instead, the fibrous material of the prefilter is sized to remove gross clots and aggregations present in the blood. The fibrous material of the postfilter is sized to provide a fluid manifold effect at the outlet of the filter. In a representative embodiment, the prefilter material has a pore size of between about 15 $\mu$m to about 20 $\mu$m, and the postfilter material has a pore size of about 20 $\mu$m. The main filter region is made of a fibrous material (e.g., polyethylene) having a pore size and diameter sized to remove leukocytes by depth filtration. The material of the main filter region can have the characteristics described in Watanabe et al. U.S. Pat. No. 4,701,267 or Nishimura et al. U.S. Pat. No. 4,936,998, which are incorporated herein by reference.

As disclosed, the filtration medium 28 can be made symmetric, meaning that the material layers of filtration medium encountered during flow through the medium 28 are the same regardless of the direction of flow. Thus, either side of the medium 28 can serve as an inlet or an outlet. The symmetric nature of the filtration medium 28 further simplifies manufacture, as it is not necessary to differentiate between "inlet" and "outlet" side of the filtration medium 28 or "inlet" or "outlet" orientation of the sheets 32 and 34.

According to the invention, a unitary, continuous peripheral seal 36 is formed by the application of pressure and radio frequency heating in a single process to the two sheets 32 and 34 and filtration medium 28. The seal 36 joins the two sheets 32 and 34 to each other, as well as joins the filtration medium 28 to the two sheets 32 and 34. The seal 36 integrates the material of the filtration medium 28 and the material of the plastic sheets 32 and 34, for a reliable, robust, leak-proof boundary. Since the seal 36 is unitary and continuous, the possibility of blood shunting around the periphery of the filtration medium 30 is eliminated.

Figure 3:
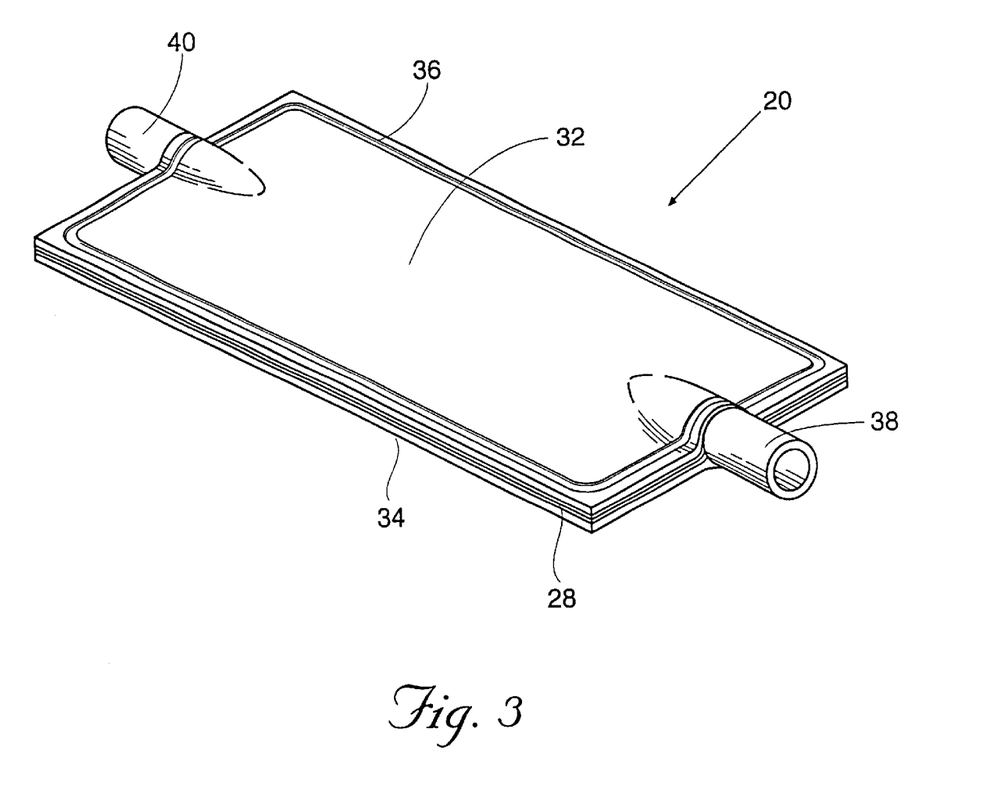
FIG. 3 is an assembled perspective view of the integral flexible filter shown in FIG. 2.

The filter 20 also includes inlet and outlet ports 38 and 40. The ports 38 and 40 comprise tubes made of medical grade plastic material, like PVC-DEHP. As FIG. 3 shows, the ports 38 and 40 can be located in the integrated peripheral seal 36, and be sealed in place at the same time that the unitary peripheral seal 36 is formed. Alternatively (see FIG. 4), the ports 38 and 40 can be inserted and sealed to each sheet 32 and 34 in a separate assembly process before the unitary peripheral seal is formed, in the manner shown in Fischer et al. U.S. Pat. No. 5,507,904. Still alternatively, the ports 38 and 40 can comprise separately molded parts that are heat sealed by radio frequency energy over a hole formed in the sheets.

Figure 4:
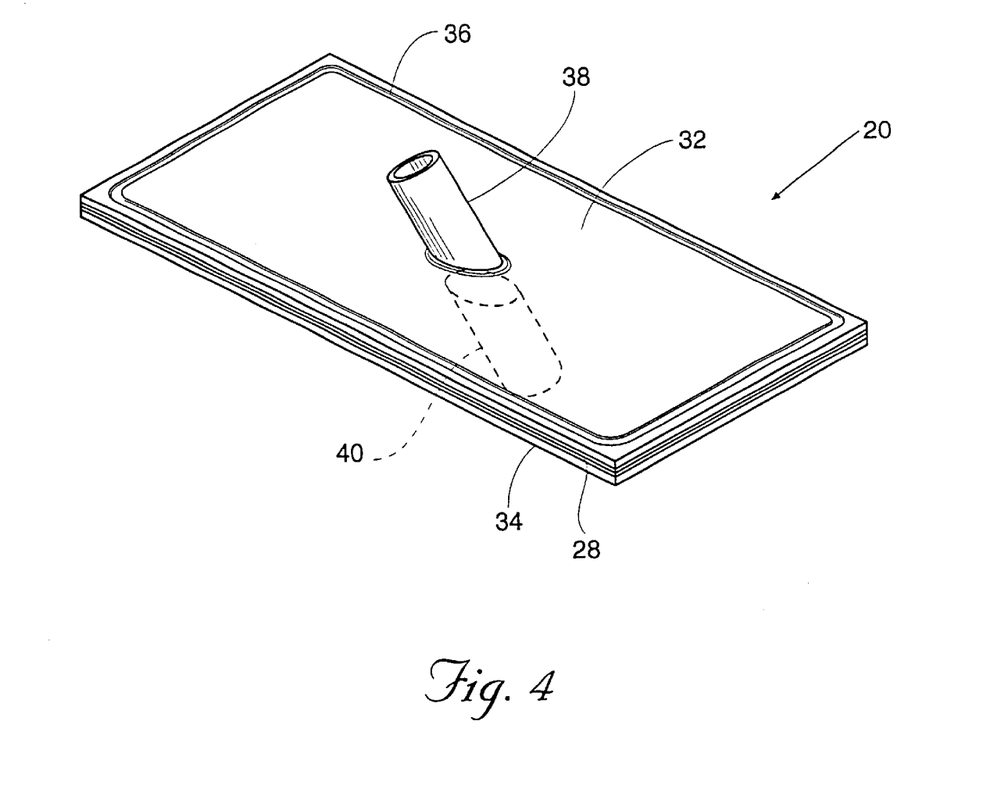
FIG. 4 is an assembled perspective view of an alternative embodiment of an integral flexible filter that can form a part of the system shown in FIG. 1, showing inlet and outlet ports that do not pass through the unitary peripheral seal.

The symmetric orientation of filtration medium 28, described above, makes the filter 30 "non-directional." The port 38 can be oriented to serve either as an inlet port or an outlet port, with the other port 40 serving, respectively, as the corresponding outlet port or inlet port, and vice versa.

Figure 5:
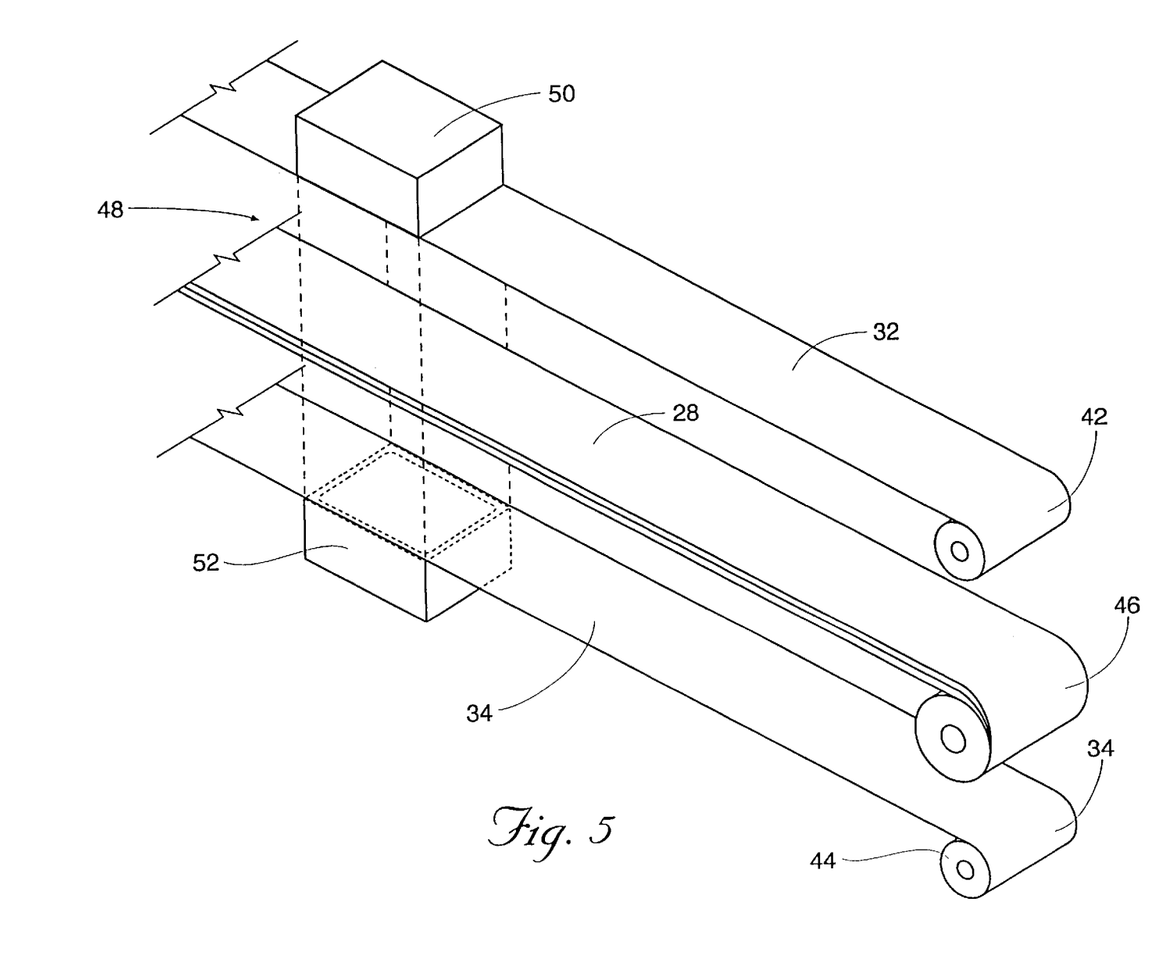
FIG. 5 is a perspective diagrammatic view showing a pre-assembled form of the integral flexible filter shown in FIG. 2, being assembled from continuous roll stock.

The filter 20 (see FIG. 5) is formed from roll stock 42 and 44 of the first and second plastic sheets 32. The layer or layers of filtration medium 28 are also supplied from roll stock 46. The roll stock 42, 44, and 46 supply a continuous, layered filter pre-assembly 48. The pre-assembly 48 is advanced in measured steps between a pair of opposed dies 50 and 52 (see FIG. 6). Between each step, the opposed dies 50 and 52 are moved together (see FIG. 7), to apply pressure to press the peripheral edge of the pre-assembly 48 together. Preferably a stop 54 is provided to accurately space the dies 50 and 52 apart from each other.

Figure 7:
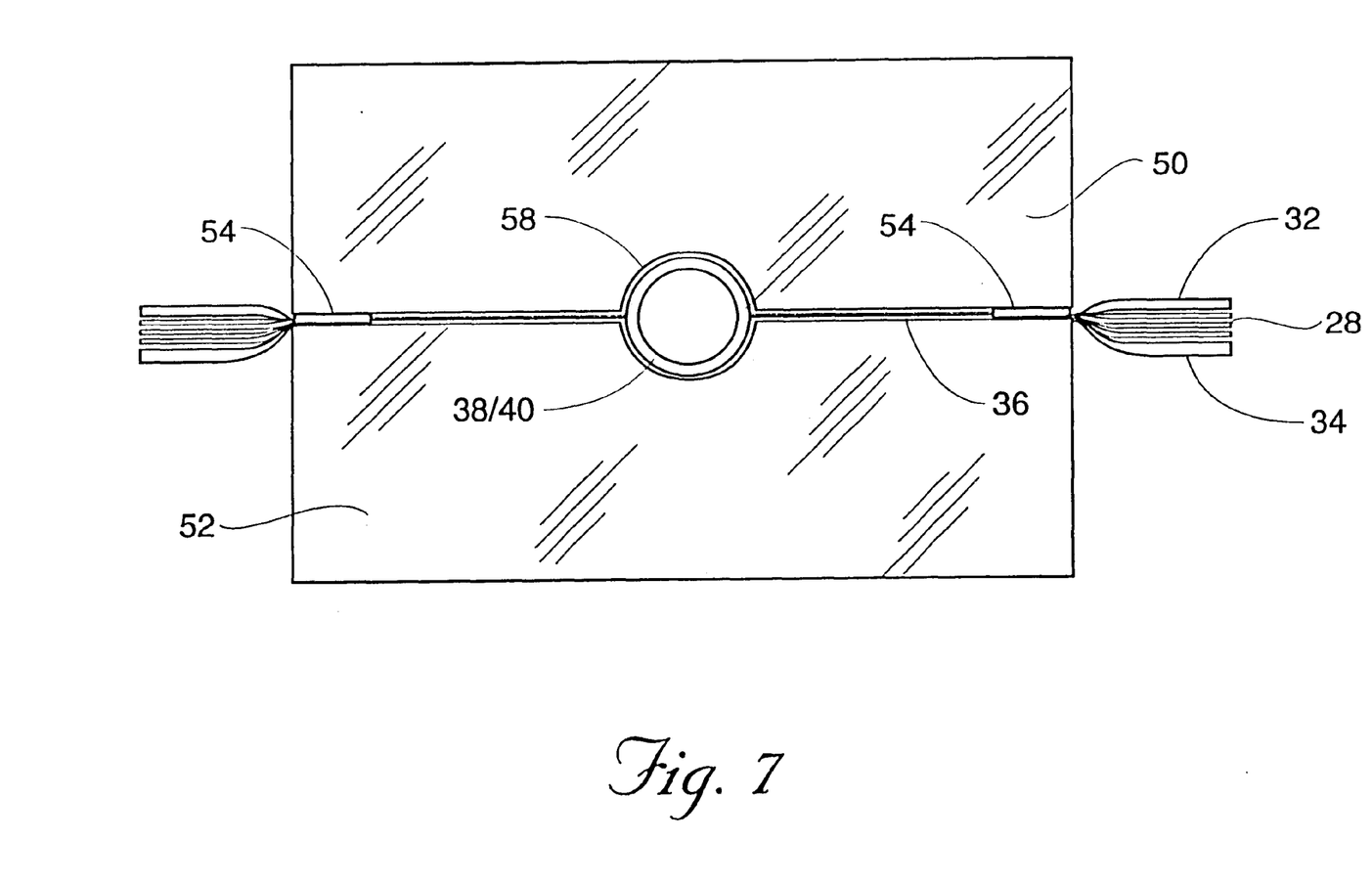
FIG. 7 is a side section view of the preassembled form of the integral flexible filter shown in FIG. 6, engaged by the dies, which apply radio frequency energy to form a unitary peripheral seal.

As the dies 50 and 52 apply pressure about the peripheral edge, RF energy is applied through the dies 50 and 52, The combination of RF energy and pressure softens the plastic material of the sheets 32 and 34. The applied pressure causes the heat softened material of the sheets 32, 34 to penetrate the interstices of the filtration medium 28, creating an interior matrix of sheet material commingled with filtration medium material. Within the matrix, the filtration medium melts, creating a composite seal 36.

At its surface, along the sheets 32 and 34, the seal 36 comprises mostly the material of the sheets 32 and 34. With increasing distance from the surface, the seal 36 comprises a commingled melted matrix of the material of the sheets 32 and 34 and the material of the filtration medium 28. This is believed to occur because the sheet material, which is electrically heated and caused to flow by the applied radio frequency energy, is further caused by the applied pressure to flow into and penetrate the interstices of the medium 28. The heated sheet material that flows under pressure into the interstices of the medium 28 causes the medium 28 itself to melt about it.

After a brief period of cooling, the seal 36 sets and the dies 50 and 52 are withdrawn. In a representative embodiment, the dies 50 and 52 are coupled to a 4 KW radio frequency energy generator. Pressure of 60 PSI is applied, maintaining a die gap of 1.2 mm. A sealing time of about 5.5 seconds is realized, followed by a cooling time of about 5 seconds.

Figure 8:
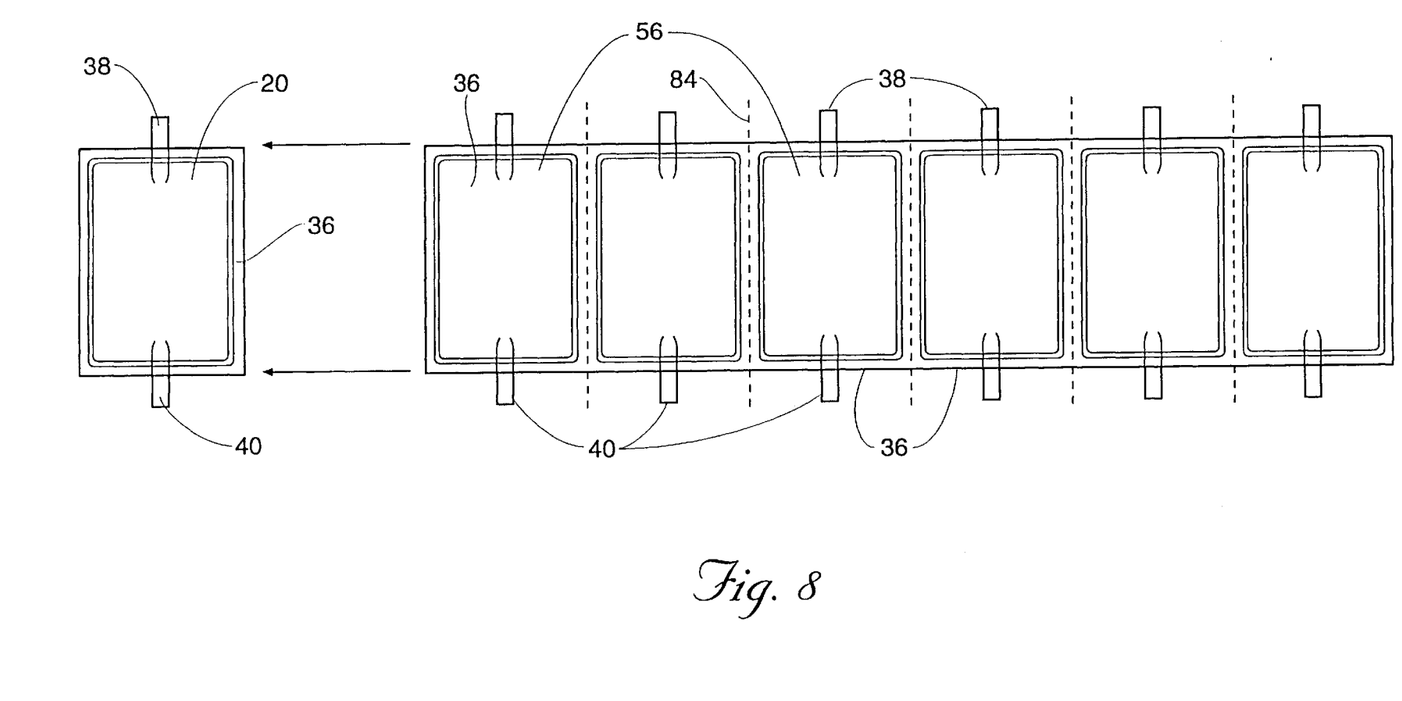
FIG. 8 is a top view of multiple sealed filter assemblies that are sequentially formed and die cut into individual filters 20 that can be integrated into the system shown in FIG. 1.

As FIG. 8 shows, multiple sealed filter assemblies 56 can be sequentially formed along the pre-assembly 48. The filter assemblies are die cut into individual filters 20 (as shown by phantom lines 84 in FIG. 8). The filter 20 is then integrated into a blood processing and collection system 10, as shown in FIG. 1.

Figure 6:
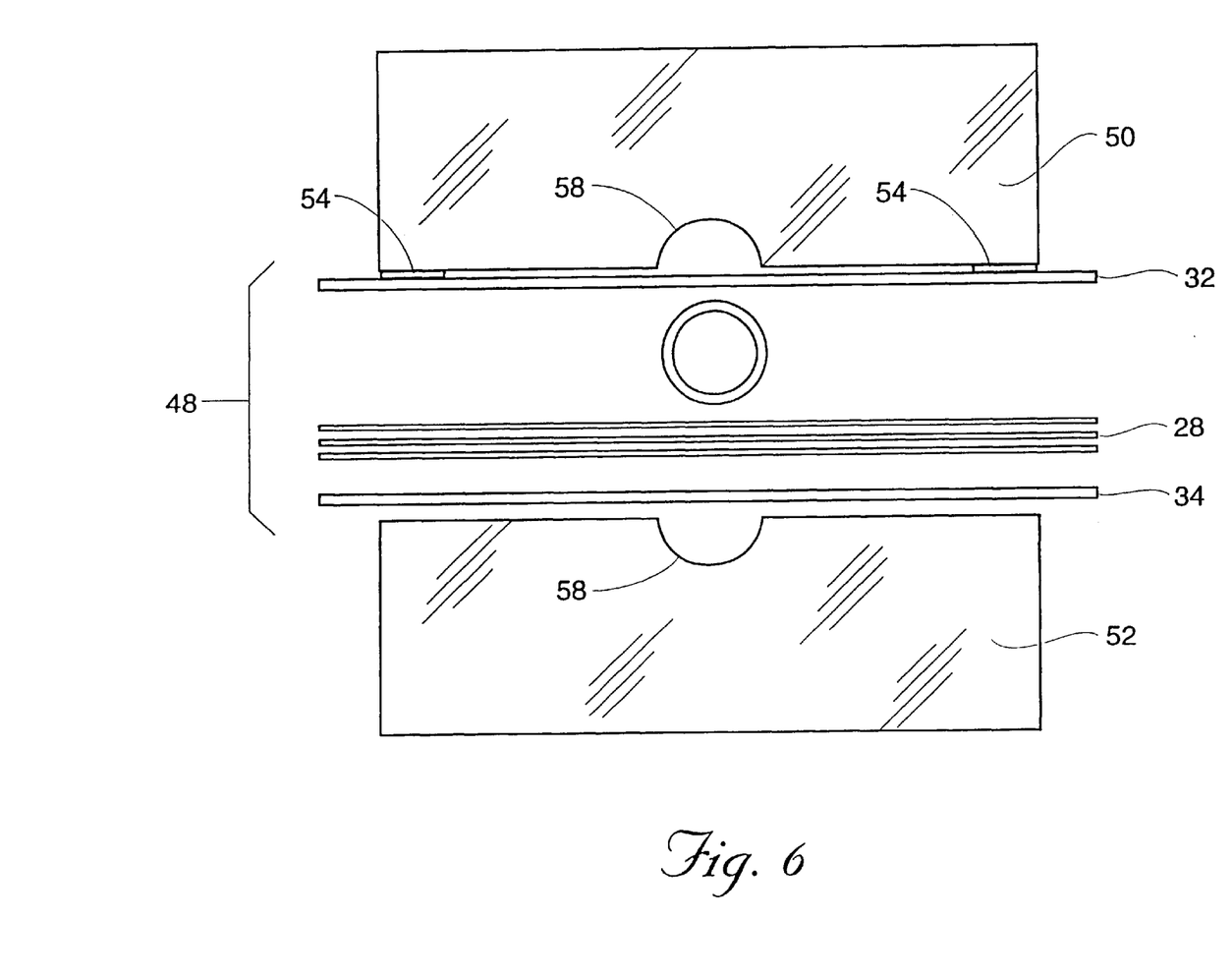
FIG. 6 is a side section view of the preassembled form of the integral flexible filter shown in FIG. 5, as it passes between two spaced apart radio frequency energy dies.

As FIGS. 6 and 7 show, when the port tubes 38 and 40 are to be located within the peripheral seal 36, the dies 50 and 52 can be provided with aligned concave recesses 58. The recesses 58 register to receive the port tubes 38 and 40. The dies 50 and 52 are brought together about the port tubes 38 and 40 and along the remaining periphery of the pre-assembly 48. Mandrels (not shown) are inserted into the tubes 38 and 40 to prevent deformation of the tubes 38 and 40 while the seal 36 forms. The mandrels are removed after the seal 36 cools.

Once integrated into the system 10, the flexible filter housing 30 comprises a variable volume reservoir that can be used, after filtration, to receive residual air trapped in the transfer bag 18. In this arrangement, after leukocyte-depleted red blood cells have been transferred from the filter 20 into the bag 18, residual air is expressed from the transfer bag 18 back into the filter housing 30. Tubing upstream of the filter 20 can be clamped closed to trap air in the filter housing 30. Being flexible, the housing 30 expands to accommodate the residual air volume.

Alternatively, the residual air in the transfer bag 18 can be transferred back into the primary bag 12 through an air vent path that bypasses the filter 20. For example, as FIG. 1 shows, a tubing path 60 leads from the transfer bag 18 to the primary bag 12, through which residual air can be vented out of the transfer bag 18.

Figure 9:
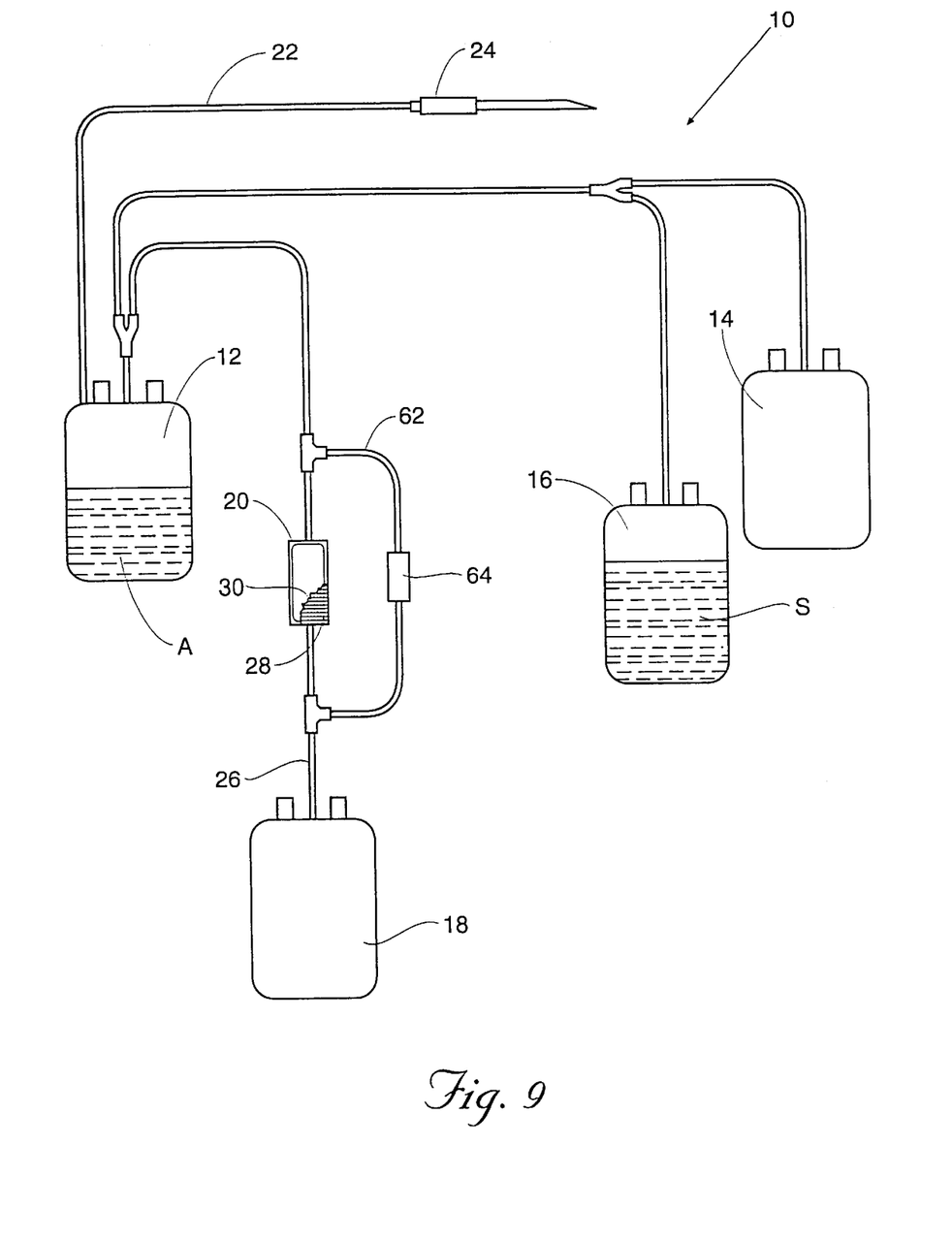
FIG. 9 is a schematic view of a blood collection and storage system that includes an integral flexible filter that removes leukocytes from red blood cells, with a by pass channel for venting air around the filter.
Figure 10:
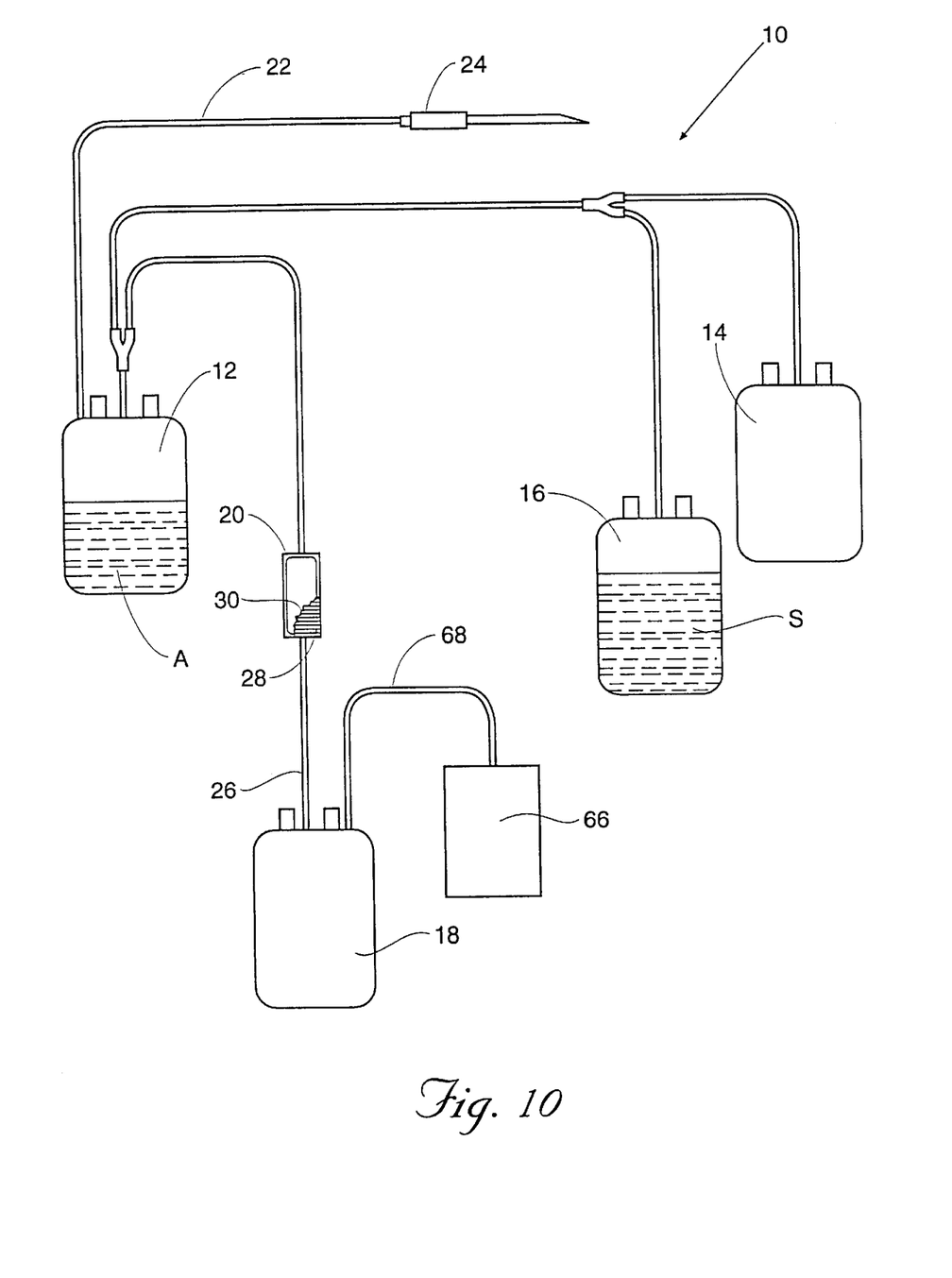
FIG. 10 is a schematic view of a blood collection and storage system that includes an integral flexible filter that removes leukocytes from red blood cells, with an integral air venting bag.

Instead of the tubing path 60 (see FIG. 9), an air bypass channel 62 can be provided around the filter 20. An in-line one-way valve 64 can be placed in the bypass channel 62, to prevent blood flow through the channel in the direction toward the transfer bag 18. In another alternative arrangement (see FIG. 10), residual air in the transfer bag 18 can be transferred into an air vent bag 66 through an integral air vent tube 68.

Figure 11:
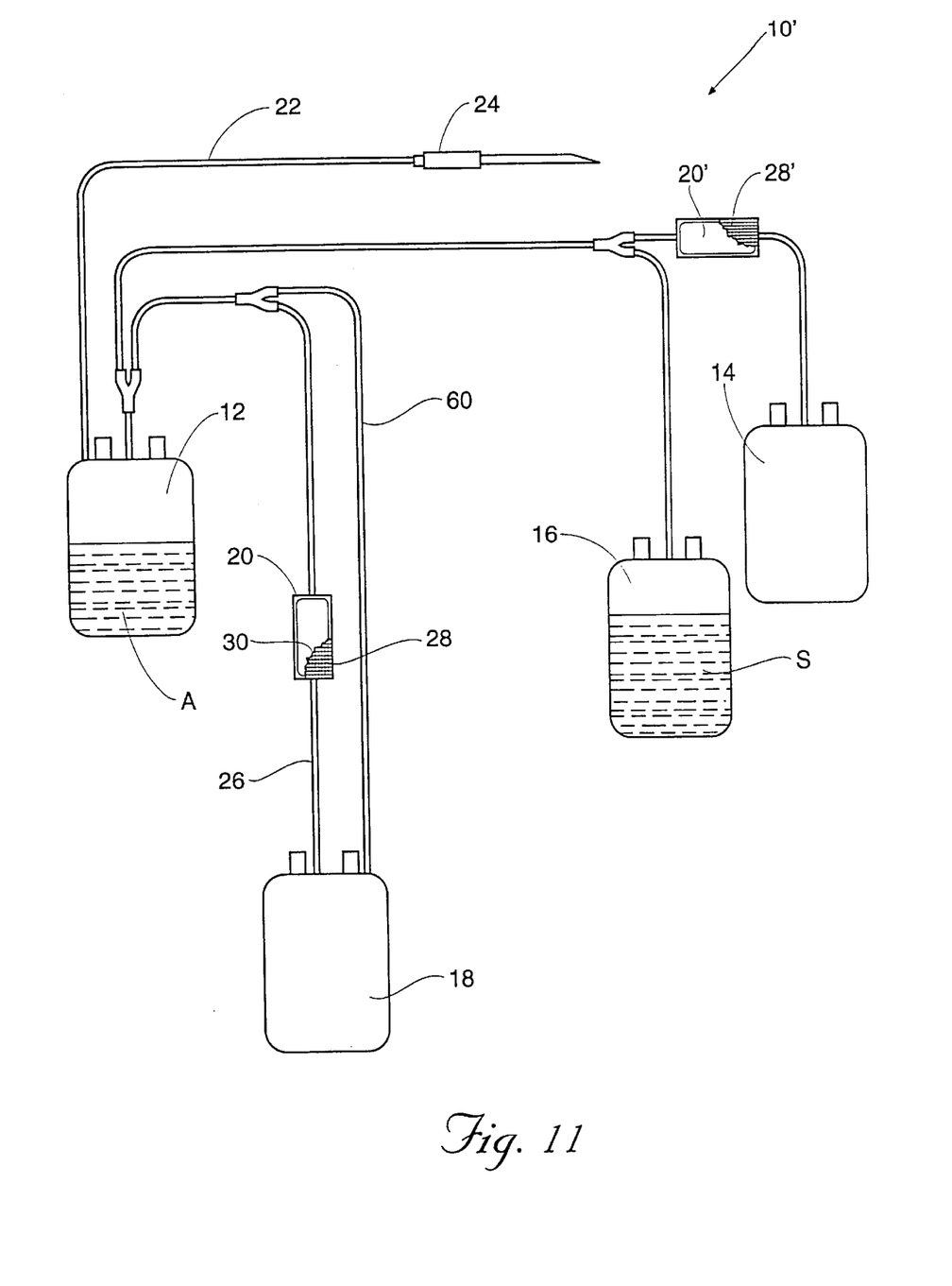
FIG. 11 is a schematic view of a blood collection and storage system that includes two integral flexible filters, one to remove leukocytes from red blood cells and the other to remove leukocytes from platelet-rich plasma.

A flexible filter can be integrated in different ways into multiple blood bag systems. For example (see FIG. 11), a system 10' like that shown in FIG. 1 can include a second integral flexible filter 20' in-line between the primary bag 12 and the transfer bag 14. In this arrangement, the filtration medium 28' is selected to remove leukocytes from platelet-poor plasma prior to entering the transfer bag 14.

Figure 12:
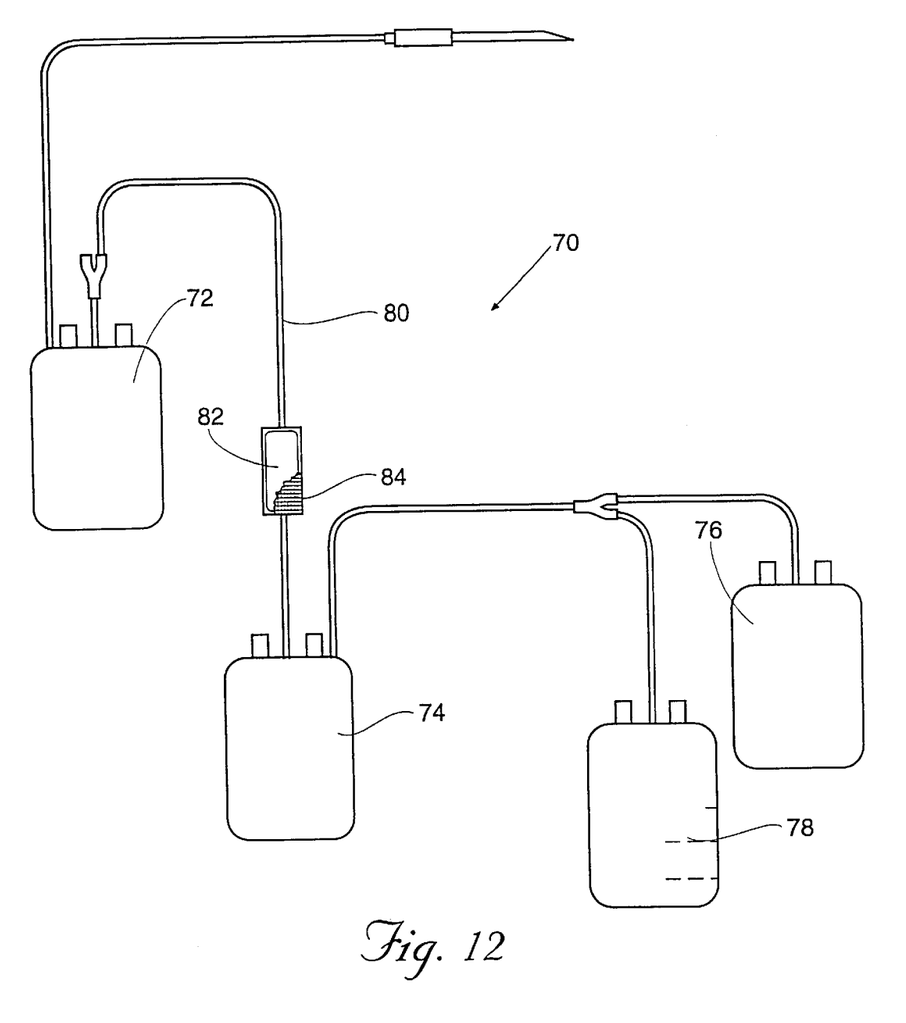
FIG. 12 is a schematic view of a blood collection and storage system that includes an integral flexible filter that removes leukocytes from whole blood prior to centrifugal processing.

As another example, FIG. 12 shows a system 70 that includes a primary bag 72 and transfer bags 74, 76, 78. The primary bag 72 receives whole blood from a donor. The whole blood is transferred from the primary bag 72 through tubing 80 into the transfer bag 74. The tubing 80 carries in-line an integral, flexible filter 82 of the type previously described. The filtration medium 84 is selected to remove leukocytes from the whole blood, without also removing platelets or red blood cells. The leukocyte-depleted whole blood is centrifugally processed in the transfer bag 74 into red blood cells and platelet-rich plasma, both of which are in a leukocyte-depleted condition.

The transfer bag 76 receives the leukocyte-depleted platelet-rich plasma, leaving the leukocyte-depleted red blood cells in the transfer bag 74 for storage. The platelet-rich plasma is centrifugally separated by conventional means in the transfer bag 76 into platelet concentrate and platelet-poor plasma. The platelet-poor plasma is transferred into the transfer bag 78 for storage. This leaves the platelet concentrate in the transfer bag 76, which serves as its storage container.

The flexible filter that embodies the invention avoids the handling and processing problems rigid filter housings have presented in the past. Unlike a rigid housing, the flexible housing 30 will not puncture associated bags, which are also made of flexible plastic materials. Unlike a rigid housing, the flexible housing 30 conforms and is compliant to stress and pressures induced during use.

The close proximity of the flexible sheet 32 and the filtration medium 28 on the inlet side of the filter 20 creates a capillary effect, which promotes displacement of air and automatic priming of the filter 30 under the fluid head pressure of gravity flow from a source container. The fluid head pressure causes the flexible sheet 32 to distend or expand after priming. It thus creates a natural pressure manifold, which evenly distributes the fluid across the inlet face of the filtration medium 28. This assures that entrapped air is vented and that the fluid flows through the filtration medium 28 under uniform pressure and distribution.

As the fluid container empties, negative pressure is created downstream of the filter 20. Because the inlet and outlet sheets 32 and 34 of the housing 30 are flexible, they will collapse around the space occupied by the filtration medium 28, minimizing the amount of residual blood left in the filter 30 after use. Fluid drains from the outlet side without the use of an auxiliary air vent.

By the same process, the flexible filter 30 provides a visual indication of an upstream occlusion or blockage during use. If an occlusion occurs in the inlet tubing upstream of the filter 30 during use (e.g., by formation of a kink in the tubing or by formation of an in-line blood clot), the inlet and outlet sheets 32 and 34 of the housing 30 will respond by collapsing, in the same fashion occasioned by an empty source container. Thus, an unexpected collapse of the filter 30 during use visually signifies the presence of an occlusion upstream of the filter 30.

Furthermore, the flexible housing 30 will not crack during heat sterilization. The flexible housing 30 also does not impede heat penetration during heat sterilization processes. Instead, the housing 30 accommodates uniform heat penetration into the filtration medium 28. The filter 20 can undergo sterilization at the same time the entire system 10 is sterilized, making a one-step sterilization process possible.

Various features of the invention are set forth in the following claims.

We claim:

1. A blood filter device comprising first and second flexible sheets, each sheet comprising a meltable material, a filter medium comprising a prefilter layer, a main filter layer, and a postfilter layer, each layer comprising a meltable material, a peripheral seal formed by application of radio frequency heating and pressure in a single step to join the first and second flexible sheets directly to the filter medium and encapsulate the filter medium between the first and second flexible sheets, with the first flexible sheet overlying the prefilter layer, the second flexible sheet overlying the postfilter layer, and the main filter layer sandwiched between the prefilter and postfilter layers, the peripheral seal comprising a commingled melted matrix comprising material of the sheets and material of the filter medium, an inlet port located in the first flexible sheet spaced from the peripheral seal for conveying blood to the filter medium, and an outlet port located in the second flexible sheet spaced from the peripheral seal for conveying blood from the filter medium.

2. A blood filter device according to claim 1 wherein the meltable material of the main filter layer serves to remove leukocytes from blood by depth filtration.

3. A blood filter device according to claim 1 wherein the meltable material of the prefilter layer serves to remove aggregations present in blood.

4. A blood collection system comprising a container for holding blood, a blood filter device as defined in claim 1 or 2 or 3, and tubing connecting the blood filter device to the container.

5. A blood filter assembly comprising a plurality of blood filter devices, each as defined in claim 1, arranged in series in an adjacent side-by-side relationship.

* * * * *